US006916954B2

(12) United States Patent
Schäfer et al.

(10) Patent No.: US 6,916,954 B2
(45) Date of Patent: Jul. 12, 2005

(54) CATALYST SYSTEM AND METHOD FOR CARBONYLATION

(75) Inventors: Martin Schäfer, Grünstadt (DE); Michael Slany, Kirchheim (DE); Edgar Zeller, Mannheim (DE); Michael Röper, Wachenheim (DE); Michael Schulz, Worms (DE); Günther Grimm, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 133 days.

(21) Appl. No.: 10/381,365

(22) PCT Filed: Sep. 25, 2001

(86) PCT No.: PCT/EP01/11052

§ 371 (c)(1),
(2), (4) Date: Mar. 25, 2003

(87) PCT Pub. No.: WO02/26382

PCT Pub. Date: Apr. 4, 2002

(65) Prior Publication Data

US 2003/0191339 A1 Oct. 9, 2003

(30) Foreign Application Priority Data

Sep. 29, 2000 (DE) .......................................... 100 48 874

(51) Int. Cl.[7] .......................... C07C 51/10; C07C 51/14; B01J 31/00
(52) U.S. Cl. ....................... 562/517; 562/521; 562/522; 502/159; 502/162; 502/200; 502/213
(58) Field of Search ................. 562/517, 521, 562/522; 564/512; 502/159, 162, 200

(56) References Cited

U.S. PATENT DOCUMENTS

| | | | | |
|---|---|---|---|---|
| 3,168,553 A | * | 2/1965 | Slaugh .......................... 560/233 |
| 3,437,676 A | * | 4/1969 | Bittler et al. ................ 560/114 |
| 3,907,701 A | | 9/1975 | Liebold et al. ............. 252/344 |
| 3,997,472 A | * | 12/1976 | O'Driscoll et al. .......... 502/159 |
| 4,127,506 A | | 11/1978 | Gray et al. .................. 252/431 |
| 4,419,490 A | | 12/1983 | Bayer et al. .................. 525/61 |
| 5,846,453 A | | 12/1998 | Mohr et al. .................. 252/331 |

FOREIGN PATENT DOCUMENTS

| | | |
|---|---|---|
| DE | 37 27 704 | 3/1989 |
| EP | 8 407 | 3/1980 |
| EP | 055 875 | 7/1982 |
| EP | 106 379 | 4/1984 |
| EP | 274 795 | 7/1988 |
| EP | 279 477 | 8/1988 |
| EP | 282 142 | 9/1988 |
| EP | 386 833 | 9/1990 |
| EP | 441 446 | 8/1991 |
| EP | 495 547 | 7/1992 |
| EP | 495 548 | 7/1992 |
| EP | 499 329 | 8/1992 |
| EP | 577 204 | 1/1994 |
| EP | 577 205 | 1/1994 |
| WO | 94/18154 | 8/1994 |
| WO | 96/19434 | 6/1996 |
| WO | 98/42717 | 10/1998 |
| WO | 98/45040 | 10/1998 |
| WO | 10/10551 | 2/2001 |

OTHER PUBLICATIONS

J.Mol.Cat., Chem 143 (1999 (23–30, Bertoux et al.
J.Chem.Soc.Perkin Trans.1, 1998 1643–1655, Adler et al.

* cited by examiner

*Primary Examiner*—S. Kumar
*Assistant Examiner*—Sikarl A. Witherspoon
(74) *Attorney, Agent, or Firm*—Keil & Weinkauf

(57) ABSTRACT

The invention relates to a catalyst system for carbonylating olefinically or acetylenically unsaturated compounds with carbon monoxide and a nucleophile compound, containing (a) palladium; (b) a phosphine and (c) a polymer containing nitrogen which is soluble in the reaction mixture, with the exception of polyvinyl polymers with aromatic radicals containing nitrogen on the polymer chain. The invention also relates to a method for carbonylation in the presence of one such catalyst system.

11 Claims, 2 Drawing Sheets

CATALYST SYSTEM AND METHOD FOR CARBONYLATION

The present invention relates to a catalyst system for the carbonylation of olefinically or acetylenically unsaturated compounds by means of carbon monoxide and a nucleophilic compound, comprising (a) palladium,
(b) a phosphine, and
(c) a nitrogen-containing polymer which is solubilizable in the reaction mixture, with the exception of polyvinyl polymers having aromatic nitrogen-containing radicals on the polymer chain, and a process for carrying out carbonylations in the presence of such a catalyst system.

The carbonylation of olefinically unsaturated compounds by means of carbon monoxide and a nucleophilic compound such as water, an alcohol or a carboxylic acid for preparing carboxylic acids, carboxylic esters and carboxylic anhydrides in the presence of a catalyst system comprising palladium and phosphine has been known for a long time and is described, for example, in EP-A 0 055 875. Disadvantages of this process are the high pressure of from 25 to 100 bar (2.5 to 10 MPa) required and the low reaction rate.

EP-A 0 106 379 discloses a significant increase in the reaction rate achieved by addition of a strong protic acid, e.g. a sulfonic acid. However, the addition of a protic acid as promoter has the disadvantage that it is discharged with the reaction product and, in particular, has to be separated from the reaction product.

F. Bertoux, J. Mol. Catal. A 143 (1999), pages 23 to 30, describes the carbonylation of propene to butyric acid in the presence of a catalyst system prepared by combining palladium chloride, tris(m-sulfonatophenyl)phosphine trisodium salt, hydrogen chloride and polyvinyl alcohol in water and subsequently activating this mixture under reaction conditions. The carbonylation was carried out in a two-phase system consisting of an aqueous phase and an organic, toluene-containing phase at a CO pressure of 40 atm (about 4 MPa). The polyvinyl alcohol acts as a solubilizer for the catalyst system in the two phases. Disadvantages are the presence of chloride, the high pressure of about 40 atm required and the two-phase system.

EP-A 0 274 795 discloses the carbonylation of olefins by means of carbon monoxide and water, alcohols or carboxylic acids in the presence of a palladium catalyst, an organic phosphine, an acid having a $pK_a$ of less than 2 and a stabilizer. Stabilizers mentioned are low molecular weight carboxamides such as N-methylpyrrolidone and N,N-diphenylacetamide.

WO 94/18154 describes the carbonylation of olefinically unsaturated compounds by means of carbon monoxide and an alcohol or amine as coreactant in the presence of a catalyst system comprising a palladium compound, a bidentate phosphine ligand and a basic compound. Basic compounds mentioned are nitrogen-containing, low molecular weight compounds selected from the group consisting of trialkylamines and nitrogen heterocycles, for example pyridine derivatives.

Since the above-described low molecular weight compounds are readily volatile, they are generally carried from the reaction system together with the reaction product. The isolation of the pure carbonylation product is therefore complicated.

U.S. Pat. No. 4,127,506 describes the preparation of a polymer-supported transition metal catalyst which is insoluble in the carbonylation reaction medium for hydroformylation reactions. This catalyst is prepared by photocatalyzed reaction of a starting transition metal compound and a solid polymeric support which contains amine groups within the polymer chain or bound to the polymer chain, using irradiation with UV light. According to this US patent, it is important that the polymers are insoluble in the carbonylation reaction medium and have a porous structure.

EP-A 0 441 446 describes the carbonylation of acetylenically or olefinically unsaturated compounds by means of carbon monoxide and water, alcohols or carboxylic acids in the presence of a group VIII metal, a phosphine, a protic acid and a tertiary amine. Tertiary amines disclosed are heterocyclic tertiary amines (e.g. pyridines), aliphatic tertiary amines (e.g. dialkylamines), tertiary anilines (e.g. N,N-dialkylanilines) and crosslinked polyvinylpyridine. A disadvantage of this process is the high total pressure of 50 bar (5 MPa) required.

It is an object of the present invention to find a catalyst system for the carbonylation of olefinically or acetylenically unsaturated compounds by means of carbon monoxide and a nucleophilic compound, which no longer has the above-described disadvantages, has a high catalytic activity even under mild reaction conditions, has a high stability in respect of deposition of palladium and palladium compounds and makes it possible to prepare carboxylic acids and carboxylic acid derivatives in high yields. A further object of the present invention is to find a carbonylation process using such a catalyst system.

We have found that this object is achieved by a catalyst system for the carbonylation of olefinically or acetylenically unsaturated compounds by means of carbon monoxide and a nucleophilic compound, comprising (a) palladium,
(b) a phosphine, and
(c) a nitrogen-containing polymer which is solubilizable in the reaction mixture, with the exception of polyvinyl polymers having aromatic nitrogen-containing radicals on the polymer chain.

It has surprisingly been found that nitrogen-containing polymers which are solubilizable in the reaction mixture have an excellent stabilizing effect on the catalyst complex comprising palladium and phosphine and thus inhibit deposition of palladium and palladium compounds. In addition, these polymers significantly improve the catalytic properties.

The nitrogen-containing polymers to be used in the catalyst system of the present invention can be solubilized in the reaction mixture and are also present in solubilized form under the reaction conditions. For the purposes of the present invention, the term "solubilized" refers to largely homogeneous distribution of the nitrogen-containing polymer in the reaction mixture so that it can stabilize the catalyst complex sufficiently. In general, the nitrogen-containing polymer is homogeneously dissolved or at least colloidally dispersed in the reaction mixture.

In the catalyst system of the present invention, use is made of nitrogen-containing polymers which can be solubilized in the reaction mixture and preferably contain more than 10 nitrogen atoms and have a molar mass of more than 1000 g/mol, preferably >10000 to $10^6$ g/mol, with the exception of polyvinyl polymers having aromatic nitrogen-containing radicals on the polymer chain. The nitrogen-containing polymers are generally homopolymers or copolymers of nitrogen-containing monomer units. Examples of suitable polymers are polyalkylenimines, in particular polyethylenimines; polyvinylamines having aliphatic nitrogen-containing radicals on the polymer chain; polymers of ethylenically unsaturated carboxamides such as poly(meth)acrylamides; polymers of acyclic or cyclic N-vinyl amides such as polyvinylformamide or polyvinylcaprolactam. The polymers can have different nitrogen-containing monomers and, if desired, nitrogen-free monomers in one molecule. The nitrogen atoms may be present in the main chain or in side groups.

The polarity of the nitrogen-containing polymer is chosen so that the polymer is solubilized in the reaction mixture under the reaction conditions. In general, the nitrogen-containing polymers are converted into derivatives to set a suitable polarity. In the case of polymers containing amino groups, they bear, for example, substituents such as alkyl, aryl, acyl or polyoxyalkylene groups on some or all of the amino groups. Substituents can be introduced by reaction with suitable derivative-forming reagents such as carboxylic acids, carboxylic acid derivatives, alkylating agents or alkene oxides, by phosphonomethylation, Strecker synthesis, etc. The reaction to form derivatives can occur on nitrogen atoms or on other positions in the polymer. Functional groups can be introduced by polymer-analogous reaction of the nitrogen-containing polymer or at the stage of the parent monomers or by concomitant use of suitable copolymerizable nitrogen-free monomers.

Preference is given to using polyethylenimines as solubilizable nitrogen-containing polymers. They preferably comprise polyethylenimine units of the formula (I) or branched isomers thereof

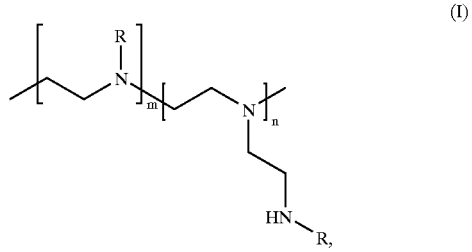

where the sum m+n is at least 10 and R are, independently of one another, hydrogen, alkyl, cycloalkyl, aryl, aralkyl and acyl radicals having up to 30 carbon atoms or hydroxyalkyl (poly)oxyalkylene radicals having up to 500 oxyalkylene units. The ratio m/(m+n) is preferably from 0.01 to 1.

The solubilized nitrogen-containing polymers (I) generally contain primary (—NH$_2$), secondary (>NH) and tertiary (>N—) amino groups. The ratio of primary:secondary:tertiary amino groups is generally 1:0.1 to 2:0.1 to 2 and preferably 1:0.8 to 1.3:0.6 to 1.1.

Preferred alkyl, cycloalkyl, aryl, aralkyl and acyl radicals are unbranched or branched, substituted or unsubstituted $C_1$–$C_{20}$-alkyl, $C_5$–$C_{10}$-cycloalkyl, $C_6$–$C_{10}$-aryl, $C_7$–$C_{10}$-aralkyl and $C_2$–$C_{21}$-acyl radicals, for example methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 3-methyl-2-butyl, 2-methyl-2-butyl, 1-hexyl, 1-heptyl, 1-octyl, 2-ethyl-1-hexyl, 1-nonyl, 1-decyl, 1-dodecyl, 1-tetradecyl, 1-hexadecyl, 1-octadecyl, 1-eicosyl, cyclopentyl, cyclohexyl, cyclooctyl, phenyl, 2-methylphenyl (2-tolyl), 3-methylphenyl (3-tolyl), 4-methylphenyl (4-tolyl), 2,4-dimethylphenyl, 2,6-dimethylphenyl, 2,4,6-trimethylphenyl, 1-naphthyl, 2-naphthyl and phenylmethyl (benzyl).

Preferred oxyalkylene units are $C_2$–$C_6$-oxyalkylene units such as oxyethylene, oxypropylene, oxybutylene, oxypentylene and oxyhexylene.

Particular preference is given to using polyethylenimines (I) or branched isomers thereof in which the radicals R are, independently of one another, hydrogen and acyl radicals having up to 30 carbon atoms. The particularly preferred polyethylenimines (I) comprise the following structural elements (II) or branched isomers thereof

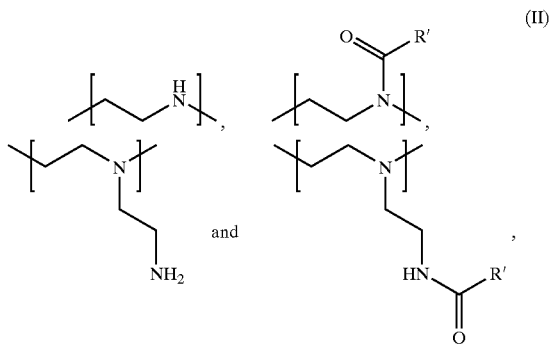

where R' are each, independently of one another, alkyl having from 1 to 29 carbon atoms.

Preferred alkyl radicals R' are branched or unbranched, substituted or unsubstituted $C_1$–$C_{21}$-alkyl radicals, for example methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 1-hexyl, 1-heptyl, 2-heptyl, 3-heptyl, 1-octyl, 2,4,4-trimethylpentyl, 1-nonyl, 2-methyl-2-octyl, 1-decyl, 1-undecyl, 1-dodecyl, 1-tridecyl, 1-tetradecyl, 1-pentadecyl, 1-hexadecyl, 1-heptadecyl, 1-octadecyl, 1-nonadecyl, 1-eicosyl and 1-henicosyl.

Further solubilizable nitrogen-containing polymers which are particularly preferably used in the catalyst system of the present invention are polyethylenimines (I) comprising, as characteristic structural elements, units of the formula (III) or branched isomers thereof

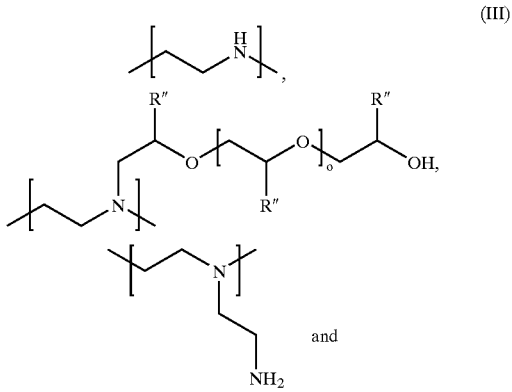

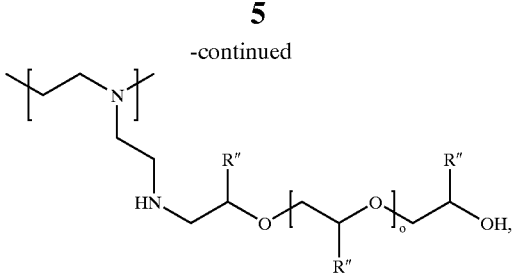

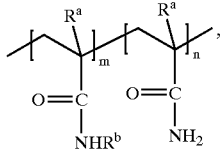

where R″ is hydrogen or $C_1$–$C_4$-alkyl and o can be from 0 to 500. These compounds are referred to as alkoxylated polyethylenimines and are described, for example, in U.S. Pat. No. 5,846,453 and U.S. Pat. No. 3,907,701. The disclosures of this earlier literature, especially in respect of the preparation of the polyamines, are hereby expressly incorporated by reference into the present application.

The structures shown in the formulae (I) to (III) above are idealized formulae for the case where the polyethylenimines depicted are linear. The repeating units can be present in any order, for example a random order. The polyethylenimine polymers to be used in the catalyst system of the present invention may also be partly branched and have, for example, structural elements of the type shown below:

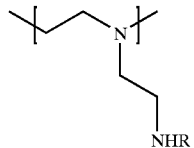

If the term "branched isomers" is hereinafter employed in connection with polyethylenimines, it refers to structural isomers derived from the structure shown by insertion of one or more of the repeating units shown in brackets in the formulae (I) to (III) between one or more NH bonds. They are branched via tertiary nitrogen atoms.

Further compounds suitable as component (c) in the catalyst system of the present invention are derivatives of polyvinylamine which have aliphatic nitrogen-containing groups on the polymer chain and comprise, as characteristic structural element, units of the formula (IV)

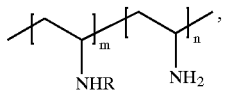

where m and n are as defined above and R are each, independently of one another, an unbranched or branched, unsubstituted or substituted, aliphatic alkyl, cycloalkyl or acyl radical having up to 30 carbon atoms or a hydroxyalkyl (poly)oxyalkylene radical having up to 500 okyalkylene units, preferably with from 2 to 6 carbon atoms per oxyalkylene unit.

Further compounds suitable as component (c) in the catalyst system of the present invention are derivatives of polyacrylamide which comprise, as characteristic structural elements, units of the formula (V)

where $R^a$ is hydrogen or methyl, $R^b$ are identical or different alkyl, cycloalkyl, aryl, aralkyl radicals having up to 30 carbon atoms, and m and n are as defined above.

The molecular weight of the polyamine derivatives to be used in the catalyst system of the present invention is at least 1000 g/mol, preferably more than 10000 g/mol. These figures refer to a mean molar mass, since a broad molecular weight distribution results, as usual, from the preparation of the polyamines and further reactions.

In general, preference is given to solubilizable nitrogen-containing polymers which are free of sulfonic acid groups.

Polyethylenimines are generally prepared by homopolymerization or copolymerization of aziridine, with or without other monomers such as vinyl amides, vinyl amines, acrylamides, acrylamines, acrylic esters, methacrylic esters and olefins such as ethene, propene, butene or butadiene, and have a mean molecular weight of from 200 to $2 \cdot 10^6$ g/mol.

The particularly preferred acylated polyethylenimines (II) are generally obtained by reacting the polyethylenimines with carboxylic acids, for example formic acid, acetic acid, propionic acid, butyric acid, valeric acid, lauric acid, 2-ethylhexanoic acid, or natural $C_{18}$-fatty acids, with the degree of amidation being from 1 to almost 100%, preferably from 30 to almost 100%, based on the amino groups which can be amidated. Details of the preparation may be found in DE-A 37 27 704. However, it is also possible to prepare the acylated polyethylenimines (II) in situ under the carbonylation reaction conditions, for example by reacting a polyethylenimine with an olefin and carbon monoxide in the presence of the nucleophilic compound, the palladium component and the phosphine or by reacting the polyethylenimine with the carboxylic acid used as solvent under the conditions of the carbonylation reaction.

The particularly preferred polyalkoxylated polyethylenimines (III) are generally prepared by reacting the polyethylenimines with up to 500 mol of ethylene oxide, propylene oxide or butylene oxide per monomer unit of the polyethylenimine. Details of the preparation may be found in U.S. Pat. No. 5,846,453.

In the catalyst system of the present invention, very particular preference is given to the acylated polyethylenimines (I) which comprise the structural elements (II) or their branched isomers where R' are each, independently of one another, $C_2$–$C_6$-alkyl such as methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 3-methyl-2-butyl or 2-methyl-2-butyl and the sum m+n is at least 50, in particular at least 100.

In particular, the catalyst system of the present invention comprises acylated polyethylenimines (II) or their branched isomers in which the acyl radicals —CO—R' are acyl groups which correspond to the carboxylic acid derivative to be prepared.

The catalyst system of the present invention generally contains from 0.5 to 15% by weight, preferably from 1 to 10% by weight and particularly preferably from 3 to 7.5% by weight, of solubilizable nitrogen-containing polymer, based on the total mass of the reaction mixture.

Phosphines suitable for the catalyst system of the present invention are described, for example, in EP-A 0 274 795, EP-A 0 282 142, EP-A 0 386 833, EP-A 0 441 446, EP-A 0 495 547, EP-A 0 495 548, EP-A 0 499 329, EP-A 0 577 204, EP-A 0 577 205, WO 94/18154, WO 96/19434, WO 96/45040 and WO 98/42717, which are hereby expressly incorporated by reference. The suitable phosphines can be represented by the formula (VI)

$$PR^1R^2R^3 \quad \text{(VI)},$$

where the radicals $R^1$, $R^2$ and $R^3$ are each, independently of one another, a carbon-containing organic radical. The radicals $R^1$, $R^2$ and/or $R^3$ can also be joined to one another.

For the purposes of the present invention, a carbon-containing organic radical is an unsubstituted or substituted, aliphatic, aromatic or araliphatic radical having from 1 to 30 carbon atoms. This radical can contain one or more heteroatoms such as oxygen, nitrogen, sulfur or phosphorus, for example —O—, —S—, —NR—, —CO—, —N=, —SiR$_2$—, —PR— and/or —PR$_2$ and/or be substituted by one or more functional groups comprising for example oxygen, nitrogen, sulfur and/or halogen, for example by fluorine, chlorine, bromine, iodine and/or a cyano group (the radical R here is likewise a carbon-containing organic radical). If the carbon-containing organic radical contains one or more heteroatoms, it can also be bound via a heteroatom. Thus, for example, ether, thioether and tertiary amino groups are also encompassed. The carbon-containing organic radical may be a monovalent or polyvalent, for example divalent, radical.

If the phosphine (VI) contains precisely one phosphorus atom, i.e. the radicals $R^1$, $R^2$ and $R^3$ contain neither a —PR— group nor a —PR$_2$ group, it will hereinafter be referred to as a monodentate phosphine. If $R^1$, $R^2$ and/or $R^3$ contain one or more —PR— or —PR$_2$ groups, the phosphines (VI) are referred to as bidentate, tridentate, etc., in accordance with the number of phosphorus atoms.

The catalyst system of the present invention preferably comprises an at least bidentate phosphine. It can be represented by the formula (VII)

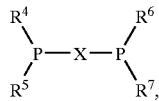

(VII)

where the radicals $R^4$, $R^5$, $R^6$ and $R^7$ are each, independently of one another, a carbon-containing organic radical and X is a carbon-containing organic bridging group. The preferred phosphines (VII) are bidentate, tridentate or tetradentate, in particular bidentate.

The term carbon-containing organic radical is as defined above.

For the purposes of the present invention, a carbon-containing organic bridging group is an unsubstituted or substituted, aliphatic, aromatic or araliphatic divalent group having from 1 to 20 carbon atoms and from 1 to 10 atoms in the chain. The organic bridging group may contain one or more heteroatoms such as oxygen, nitrogen, sulfur or phosphorus, for example —O—, —S—, —NR—, —CO—, —N=, —SiR$_2$—, —PR— and/or —PR$_2$, and/or be substituted by one or more functional groups comprising, for example, oxygen, nitrogen, sulfur and/or halogen, for example by fluorine, chlorine, bromine, iodine and/or a cyano group (the radical R here is likewise a carbon-containing organic radical). If the organic bridging group contains one or more heteroatoms, it can also be bound via a heteroatom. Thus, for example, ether, thioether and tertiary amino groups are also encompassed.

Monovalent radicals $R^1$, $R^2$ and $R^3$ in formula (VI) and $R^4$, $R^5$, $R^6$ and $R^7$ in formula (VII) are each preferably an unbranched or branched, acyclic or cyclic, unsubstituted or substituted alkyl radical having from 1 to 20 aliphatic carbon atoms in which one or more of the CH$_2$ groups may be replaced by heteroatoms such as —O— or —S—, or by heteroatom-containing groups such as —CO—, —NR— or —SiR$_2$— and in which one or more of the hydrogen atoms may be replaced by substituents such as aryl groups; or an unsubstituted or substituted aromatic radical having one ring or two or three fused rings, in which one or more ring atoms may be replaced by heteroatoms such as nitrogen and in which one or more of the hydrogen atoms may be replaced by substituents such as alkyl or aryl groups.

Examples of preferred monovalent radicals are unsubstituted or substituted $C_1$–$C_{20}$-alkyl, $C_5$–$C_{20}$-cycloalkyl, $C_6$–$C_{20}$-aryl and $C_3$–$C_{20}$-heteroaryl radicals, for example methyl, ethyl, 1-propyl, 2-propyl (sec-propyl), 1-butyl, 2-butyl (sec-butyl), 2-methyl-1-propyl (isobutyl), 2-methyl-2-propyl (tert-butyl), 1-pentyl, 2-pentyl, 3-pentyl, 2-methyl-2-butyl (tert-amyl), 1-hexyl, 2-hexyl, 3-hexyl, 2-methyl-2-pentyl, 3-methyl-3-pentyl, 2-methoxy-2-propyl, cyclopentyl, cyclohexyl, cyclooctyl, phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl, 2-methoxyphenyl, 3-methoxyphenyl, 4-methoxyphenyl, 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 2-(1,3,5-triazin)yl, 1-naphthyl, 2-naphthyl, 2-quinolyl, 8-quinolyl, 1-isoquinolyl and 8-isoquinolyl.

In the case of divalent radicals, $R^1$ together with $R^2$, $R^2$ together with $R^3$ or $R^1$ together with $R^3$ in formula (VI) and $R^4$ together with $R^5$ and/or $R^6$ together with $R^7$ in formula (VII) are in each case preferably an unbranched or branched, acyclic or cyclic, unsubstituted or substituted $C_4$–$C_{20}$-alkylene radical ("divalent alkyl radical") having from 4 to 10 atoms in the alkylene chain, in which the CH$_2$ groups may also be replaced by hetero groups, for example —CO—, —O—, —SiR$_2$— or —NR— and in which one or more of the hydrogen atoms may be replaced by substituents, for example aryl groups.

Examples of preferred divalent radicals are unsubstituted or substituted $C_4$–$C_{30}$-alkylene radicals in which CH$_2$ groups may be replaced by hetero groups such as —O—, for example 1,4-butylene, 1,4-dimethyl-1,4-butylene, 1,1,4,4-tetramethyl-1,4-butylene, 1,4-dimethoxy-1,4-butylene, 1,4-dimethyl-1,4-dimethoxy-1,4-butylene, 1,5-pentylene, 1,5-dimethyl-1,5-pentylene, 1,5-dimethoxy-1,5-pentylene, 1,1,5,5-tetramethyl-1,5-pentylene, 1,5-dimethyl-1,5-dimethoxy-1,5-pentylene, 3-oxa-1,5-pentylene, 3-oxa-1,5-dimethyl-1,5-pentylene, 3-oxa-1,5-dimethoxy-1,5-pentylene, 3-oxa-1,1,5,5-tetramethyl-1,5-pentylene, 3-oxa-1,5-dimethyl-1,5-dimethoxy-1,5-pentylene, 1,4-cyclooctylene, 1,5-cyclooctylene, 1,4-dimethyl-1,4-cyclooctylene, 1,4-dimethyl-1,5-cyclooctylene, 1,4-dimethyl-5,8-cyclooctylene, 1,5-dimethyl-1,4-cyclooctylene, 1,5-dimethyl-1,5-cyclooctylene, 1,5-dimethyl-4,8-cyclooctylene,

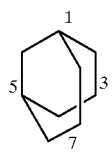

3,7-bicyclo[3.3.1]nonylene,

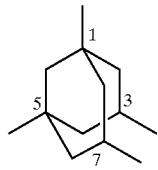

1,3,5,7-tetramethyl-3,7-bicyclo[3.3.1]nonylene,

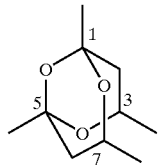

1,3,5,7-tetramethyl-4,8,9-trioxa-3,7-bicyclo[3.3.1] nonylene.

In the case of trivalent radicals, $R^1$ together with $R^2$ and $R^3$ are in each case preferably an unbranched or branched, acyclic or cyclic, unsubstituted or substituted trivalent alkyl radical having from 4 to 20 carbon atoms and in each case from 4 to 10 atoms in the chain, in which $CH_2$ groups may also be replaced by hetero groups such as —CO—, —O— or —NR— and in which one or more of the hydrogen atoms may be replaced by substituents such as aryl groups.

The phosphine (VI) or (VII) to be used in the catalyst system of the present invention particularly preferably comprises radicals $R^1$, $R^2$ and/or $R^3$ or $R^4$, $R^5$, $R^6$ and/or $R^7$, which are each, independently of one another, an unsubstituted or substituted $C_3$–$C_{12}$-alkyl radical in which at least two, preferably three, further skeletal atoms are bound to the α carbon atom, or an unsubstituted or substituted aromatic radical having 6 ring atoms in which one, two or three ring atoms may be replaced by nitrogen; and/or radicals $R^1$ together with $R^2$, $R^2$ together with $R^3$ or $R^1$ together with $R^3$ or else $R^4$ together with $R^5$ and/or $R^6$ together with $R^7$, which are in each case, independently of one another, an unsubstituted or substituted $C_4$–$C_{30}$-alkylene radical having from 4 to 7 atoms in the shortest alkylene chain, in which $CH_2$ groups may be replaced by hetero groups such as —O—.

For the present purposes, skeletal atoms are the skeleton-forming atoms, for example carbon, oxygen or nitrogen.

Examples of particularly preferred monovalent radicals $R^1$, $R^2$ and/or $R^3$ and also $R^4$, $R^5$, $R^6$ and/or $R^7$ are 2-propyl (sec-propyl), 2-butyl (sec-butyl), 2-methyl-2-propyl (tert-butyl), 2-methyl-2-butyl (tert-amyl), phenyl, 2-methylphenyl (o-tolyl), 3-methylphenyl (m-tolyl), 4-methylphenyl (p-tolyl), 2,6-dimethylphenyl, 2,4-dimethylphenyl, 2,4,6-trimethylphenyl and 2-pyridyl, in particular 2-methyl-2-propyl (tert-butyl) and phenyl. Examples of particularly preferred divalent radicals $R^1$ together with $R^2$, $R^2$ together with $R^3$ or $R^1$ together with $R^3$ and also $R^4$ together with $R^5$ and/or $R^6$ together with $R^7$ are 1,1,4,4-tetramethyl-1,4-butylene, 1,4-dimethyl-1,4-dimethoxy-1,4-butylene, 1,1,5,5-tetramethyl-1,5-pentylene, 1,5-dimethyl-1,5-dimethoxy-1,5-pentylene, 1,5-dimethyl-1,5-cyclooctylene, 1,3,5,7-tetramethyl-3,7-bicyclo[3.3.1]nonylene and 1,3,5,7-tetramethyl-4,8,9-trioxa-3,7-bicyclo[3.3.1]nonylene, in particular 1,3,5,7-tetramethyl-4,8,9-trioxa-3,7-bicyclo[3.3.1]nonylene.

The organic bridging group X in formula (VII) is preferably an unbranched or branched, acyclic or cyclic, unsubstituted or substituted divalent aliphatic, aromatic or araliphatic group having from 1 to 20 carbon atoms and from 1 to 8 atoms, preferably from 2 to 4 atoms, in the chain, in which one or more of the $CH_2$ groups may be replaced by heteroatoms such as —O—, or by heteroatom-containing groups such as —CO— or —NR—, and/or one or more of the aromatic ring atoms may be replaced by heteroatoms, for example nitrogen, and in which one or more of the hydrogen atoms may be replaced by substituents such as alkyl or aryl groups.

Examples of preferred bridging groups X are 1,2-ethylene, 1,3-propylene, 1,2-propylene, 1,4-butylene, 2-methyl-1,3-propylene, 1,5-pentylene, 2,2-dimethyl-1,3-propylene, 1,6-hexylene, —O—$CH_2CH_2$—O—, —O—$CH_2CH_2CH_2$—O—, —$CH_2$—O—$CH_2$—, —$CH_2CH_2$—O—$CH_2CH_2$—, o-phenylene, o-xylene and —$CH_2$—NR—$CH_2$—, in particular 1,2-ethylene-, 1,3-propylene-, 1,4-butylene- and o-xylene.

A particularly preferred monodentate phosphine is triphenylphosphine. As particularly preferred bidentate phosphines, mention may be made of 1,2-bis(di-tert-butylphosphino)ethane, 1,2-bis(diphenylphosphino)ethane, 1,2-P,P'-di(2-phospha-1,3,5,7-tetramethyl-6,9,10-trioxatricyclo[3.3.1.1{3.7}]decylethane ("dpa-2" for short), 1,3-bis(di-tert-butylphosphino)propane, 1,3-bis(diphenylphosphino)propane, 1,3-P,P'-di(2-phospha-1,3,5,7-tetramethyl-6,9,10-trioxatricyclo[3.3.1.1{3.7}]decylpropane ("dpa-3" for short), 1,4-bis(di-tert-butylphosphino)butane, 1,4-bis(diphenylphosphino)butane, 1,4-P,P'-di(2-phospha-1,3,5,7-tetramethyl-6,9,10-trioxatricyclo[3.3.1.1{3.7}]decylbutane ("dpa-4" for short), α,α'-bis(di-tert-butylphosphino)-o-xylene, α,α'-bis(diphenylphosphino)-o-xylene and α,α'-P,P'-di(2-phospha-1,3,5,7-tetramethyl-6,9,10-trioxatricyclo[3.3.1.1{3.7}]decyl-o-xylene, in particular 1,3-bis(di-tert-butylphosphino)propane, 1,3-bis(diphenylphosphino)propane and

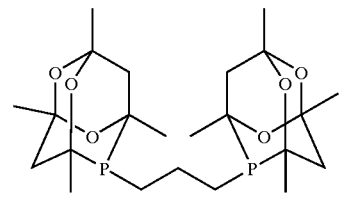

1,3-P,P'-di(2-phospha-1,3,5,7-tetramethyl-6,9,10-trioxatricyclo[3.3.1.1{3.7}]decylpropane ("dpa-3").

When using monodentate phosphine ligands, the catalyst system of the present invention generally comprises from 50 to 500 mmol, preferably from 100 to 250 mmol, of phosphine/l of reaction mixture, and when using bidentate phosphine ligands it generally comprises from 1 to 50 mmol, preferably from 2 to 25 mmol, of phosphine/l of reaction mixture.

As palladium source for the catalyst system of the present invention, it is possible to use inorganic and organic salts of palladium, palladium compounds with nitrogen-, phosphorus- and/or oxygen-containing donor ligands and also palladium applied to a support or supported palladium compounds. Preference is given to halogen-free palladium sources.

Examples of suitable inorganic and organic salts of palladium are palladium(II) nitrate, palladium(II) sulfate, palladium(II) carboxylates (for example palladium(II) acetate or palladium(II) propionate), palladium(II) sulfonates and palladium(II) acetylacetonate.

Examples of suitable palladium compounds with nitrogen-, phosphorus- and/or oxygen-containing donor ligands are tetrakis(triphenylphosphine)palladium(0) (Pd (PPh$_3$)$_4$), dibenzylideneacetone palladium(0) (Pd(dba)$_2$) or [Pd(dpa-3)(CH$_3$CN)$_2$][A]$_2$, where A is a weakly coordinated anion, for example chlorate, hexafluorophosphate, tetrafluoroborate or p-toluenesulfonate, and "dpa-3" is as defined above.

A suitable example of palladium applied to a support is palladium on activated carbon. Palladium sources of this type are preferably used as particles which can be suspended in the reaction mixture. To ensure a stable suspension, the support materials are preferably hydrophilic in nature, if necessary made hydrophilic by separate measures such as partial surface oxidation of activated carbon.

When using monodentate phosphine ligands, the catalyst system of the present invention generally comprises from 5 to 20 mmol, preferably from 5 to 10 mmol, of palladium/l of reaction mixture, and when using bidentate phosphine ligands it generally comprises from 0.5 to 5 mmol, preferably from 1 to 3 mmol, of palladium/l of reaction mixture.

The catalyst system of the present invention advantageously further comprises a protic acid (Brønsted acid) as additional component to activate the system. This can be the carboxylic acid corresponding to that formed in the carbonylation of the unsaturated compound by means of carbon monoxide and water or can be another organic or inorganic protic acid.

Suitable carboxylic acids which can be formed in the carbonylation by means of carbon monoxide and water (in-situ) are, for example, propionic acid (from ethene), butyric acid (from propene) or methacrylic acid (from propyne). The carboxylic acids, e.g. acetic acid or propionic acid, can naturally also be added to the catalyst system (ex-situ). If the catalyst system is used for the preparation of carboxylic acids, the carboxylic acid formed in-situ is frequently sufficient to achieve activation, depending on the activity of the catalyst system. The advantage of this variant is that no additional component is present in the system.

However, in many cases it is advantageous to add an additional organic or inorganic protic acid to the catalyst system of the present invention. This is, for example, the case when no carboxylic acid is present or is formed in-situ during the carbonylation (e.g. when preparing carboxylic esters) or a greater activity-increasing effect than can be obtained by means of the carboxylic acid formed in-situ is to be achieved. When using additional protic acids, protic acids having a pK$_a$ of $\leq 3$, in particular $\leq 2$, are preferred. Suitable protic acids are described, for example, in EP-A 0 106 379 and EP-A 0 279 477, which are hereby expressly incorporated by reference. Preferred protic acids having a pK$_a$ of $\leq 2$ are, for example, phosphoric acid or sulfonic acids such as p-toluenesulfonic acid, methanesulfonic acid or trifluoromethanesulfonic acid. If protic acids which do not correspond to the carboxylic acid derivative to be prepared are added, their molar ratio to the palladium used is generally from 1 to 20.

The catalyst system of the present invention can generally be obtained by combining the above-described components (a), (b), (c) and any additional protic acid in a solvent in any order, possibly with formation of intermediates such as palladium-phosphine complexes. The solvent preferably corresponds to the desired carbonylation product.

Furthermore, we have found a process for the carbonylation of olefinically or acetylenically unsaturated compounds by means of carbon monoxide and a nucleophilic compound, wherein the catalyst system of the present invention, as described above, is used.

The individual components of the catalyst system and their ratios are described above.

The process of the present invention is generally carried out at from 50 to 150° C., preferably from 80 to 150° C. and particularly preferably from 90 to 130° C. The pressure in the process of the present invention is generally from 0.1 to 5 MPa abs, preferably from 0.1 to 3 MPa abs and particularly preferably from 0.2 to 1.5 MPa abs.

Olefinically unsaturated compounds which can be used in the process of the present invention are unsubstituted or substituted alkenes having one or more carbon—carbon double bond(s). Examples of possible substituents are aryl groups, heteroaryl groups, halides or functional groups such as —COOH, —COOR, —CONR$_2$, —CN or —OR. In general, the olefinically unsaturated compounds have from 2 to 30 carbon atoms and one or two carbon—carbon double bond(s). Preferred compounds are unsubstituted $C_2$–$C_{20}$-alkenes such as ethene, propene, 1-butene, 2-butene, 1-pentene, 1-hexene, 3-hexene, 1-heptene, 3-heptene, 1-octene, 3-methyl-2-heptene, 3-methyl-3-heptene, 1-decene, cyclopentene, cyclohexene or cyclooctene;

unsubstituted $C_3$–$C_{20}$-alkadienes having cumulated, conjugated or isolated carbon—carbon double bonds, for example propadiene (allene), 1,3-butadiene, 1,3-pentadiene, 1,5-hexadiene or dicyclopentadiene; and substituted $C_3$–$C_{20}$-alkenes and alkadienes such as styrene, 1-methoxy-2-butene, 3-methoxy-1-butene, 1-butoxy-2-butene, 3-butoxy-1-butene, methyl, ethyl, propyl or butyl esters of 2-, 3- or 4-pentenoic acid or 2-, 3- or 4-pentenenitrile.

Acetylenically unsaturated compounds which can be used in the process of the present invention are unsubstituted or substituted alkynes having one or more carbon—carbon triple bond(s). In general, they have from 2 to 30 carbon atoms and one carbon—carbon triple bond. Possible substituents are those mentioned for the olefinically unsaturated compounds. Preferred compounds are unsubstituted $C_2$–$C_{20}$-alkynes such as ethyne or propyne; and substituted $C_3$–$C_{20}$-alkynes such as ethynylbenzene (phenylacetylene).

Particularly preferred unsaturated compounds are the olefinically unsaturated compounds, very particularly preferably unsubstituted $C_2$–$C_6$-alkenes, in particular ethene.

The molar ratio of carbon monoxide to the unsaturated compounds in the process of the present invention is generally from 1 to 3, preferably from 1 to 1.5, per double or triple bond.

The nucleophilic compounds used in the process of the present invention are compounds which generally have at least one mobile hydrogen atom. Suitable nucleophilic compounds are, for example, water, alcohols and/or carboxylic acids. Preferred alcohols are $C_1$–$C_{10}$-alkanols such as methanol, ethanol, 1-propanol, 2-propanol (isopropanol), 1-butanol, 2-butanol (sec-butanol), 2-methyl-1-propanol (isobutanol), 2-methyl-2-propanol (tert-butanol), 1-pentanol, 2-pentanol, 3-pentanol, 2-methyl-1-butanol, 3-methyl-1-butanol (isoamyl alcohol), 2-methyl-2-butanol (tert-amyl alcohol), 1-hexanol, 2-hexanol, 4-methyl-2-pentanol, 3,3-dimethyl-2-butanol, 1-heptanol, 1-octanol, 1-nonanol, 1-decanol, 1,2-ethylene glycol and 1,3-propylene glycol. Preferred carboxylic acids are $C_2$–$C_{20}$-carboxylic acids, particularly preferably $C_2$–$C_{10}$-carboxylic acids, for example acetic acid, propionic acid, butyric acid and methacrylic acid, in particular those carboxylic acids which are formed as carbonylation products from the reaction of the unsaturated compound with carbon monoxide and water.

In the process of the present invention, carboxylic acids are formed when using water as nucleophilic compound, carboxylic esters are formed when using alcohols and carboxylic anhydrides are formed when using carboxylic acids (which may also have been prepared in-situ by use of water).

Particular preference is given to using water and/or a $C_1$–$C_{10}$-alkanol as nucleophilic compound in the process of the present invention.

The molar ratio of the unsaturated compound to the nucleophilic compound can be varied within a very wide range in the process of the present invention. It is generally from 0.001 to 1000, preferably from 0.01 to 1.

As carboxylic acid derivatives to be prepared by the process of the present invention, preference is given to propionic acid, propionic anhydride, methyl propionate, butyl propionate and methyl methacrylate, in particular propionic acid.

The solubilizable nitrogen-containing polymer used in the process of the present invention is particularly preferably a polyethylenimine (I) in which the radicals R are acyl groups corresponding to the carboxylic acid derivative to be prepared. In the particularly preferred carbonylation of ethene, a polyethylenimine (I) which has been amidated with propionic acid is thus preferably used.

The process of the present invention is carried out in a predominantly liquid phase. The catalyst system is generally very largely homogeneously solubilized in the reaction mixture. In general, the liquid carbonylation products and the nucleophilic compounds and mixtures thereof function as solvents. However, it is also possible to carry out the carbonylation in a preferably inert solvent. Examples of suitable solvents are aromatic or aliphatic hydrocarbons such as toluene, xylenes or decalin, or polar, aprotic solvents such as tetrahydrofuran, 1,4-dioxane, N-methylpyrrolidone, N-methylpiperidone, dimethylsulfoxide, glycol ethers (e.g. 1,2-dimethoxyethane, bis(2-methoxyethyl) ether or bis(2-butoxyethyl) ether), dimethylformamide, dimethylformanilide, ethylene carbonate, propylene carbonate, ketones (e.g. acetone or diethyl ketone) or mixtures thereof. The process is preferably carried out in a solvent which corresponds to the carbonylation product, since this introduces no further extraneous components into the system.

The process of the present invention can be carried out batchwise, semicontinuously or continuously.

In a general method of preparing the catalyst system or its precursor, the components (a) palladium source, (b) phosphine, (c) nitrogen-containing polymer which is solubilizable in the reaction mixture and any protic acid to be used are combined in a solvent in any order. The solvent preferably corresponds to the desired carbonylation product.

In a general method of carrying out the carbonylation process batchwise, the catalyst system or its precursor is admixed with the starting materials unsaturated compound, nucleophilic compound and carbon monoxide in a suitable reaction apparatus (e.g. an autoclave) and the system is maintained under reaction conditions (pressure, temperature). After the reaction is complete, the reaction apparatus is cooled, vented and the reaction mixture is worked up in a customary manner, e.g. by distillation.

In a general method of carrying out the carbonylation semicontinuously, the catalyst system or its precursor is admixed, depending on the embodiment, with no, with one, two or all three starting component(s) in a suitable reaction apparatus (e.g. an autoclave) and the system is brought to the reaction conditions (temperature, pressure). To set the pressure, the gaseous starting materials carbon monoxide and/or the unsaturated compound (if gaseous) are introduced. The necessary starting materials are subsequently fed in continuously or periodically during the course of the reaction. After the reaction is complete, the reaction apparatus is cooled, vented and the reaction mixture is worked up in a customary manner, e.g. by distillation.

In a general method of carrying out the carbonylation continuously, the catalyst system or its precursor is admixed, depending on the embodiment, with no, with one, two or all three starting component(s) in a suitable reaction apparatus (e.g. an autoclave) and the system is brought to the reaction conditions (temperature, pressure). To set the pressure, the gaseous starting materials carbon monoxide and/or the unsaturated compound (if gaseous) are introduced. The three starting materials are subsequently fed in continuously at a rate corresponding to that at which they are consumed and a corresponding part of the reaction mixture is discharged continuously from the reaction apparatus for work-up.

In a preferred embodiment of the continuous preparation of propionic acid, palladium(II) acetate, the bidentate phosphine ligand "dpa-3" and a polyethylenimine polymer which has been amidated with propionic acid are dissolved in propionic acid and brought to the desired reaction temperature and to the desired reaction pressure by introduction of carbon monoxide in a suitable reaction apparatus, for example a bubble column. The continuous introduction of the three starting materials ethene, carbon monoxide and water is subsequently commenced. The propionic acid formed can then be continuously removed from the reaction apparatus, for example by stripping with a suitable gas stream (e.g. ethene/carbon monoxide mixture).

The catalyst system of the present invention has a high catalytic activity and a high stability in respect of deposition of palladium and palladium compounds. The process of the present invention using the catalyst system of the present invention makes it possible to carbonylate olefinically or acetylenically unsaturated compounds by means of carbon monoxide and a nucleophilic compound under mild reaction conditions to give carboxylic acid derivatives in high yield. The use of the nitrogen-containing polymer also makes it possible to separate the carbonylation product from the reaction mixture in a technically simple manner, which is a decisive advantage.

EXAMPLES

Figure 1:
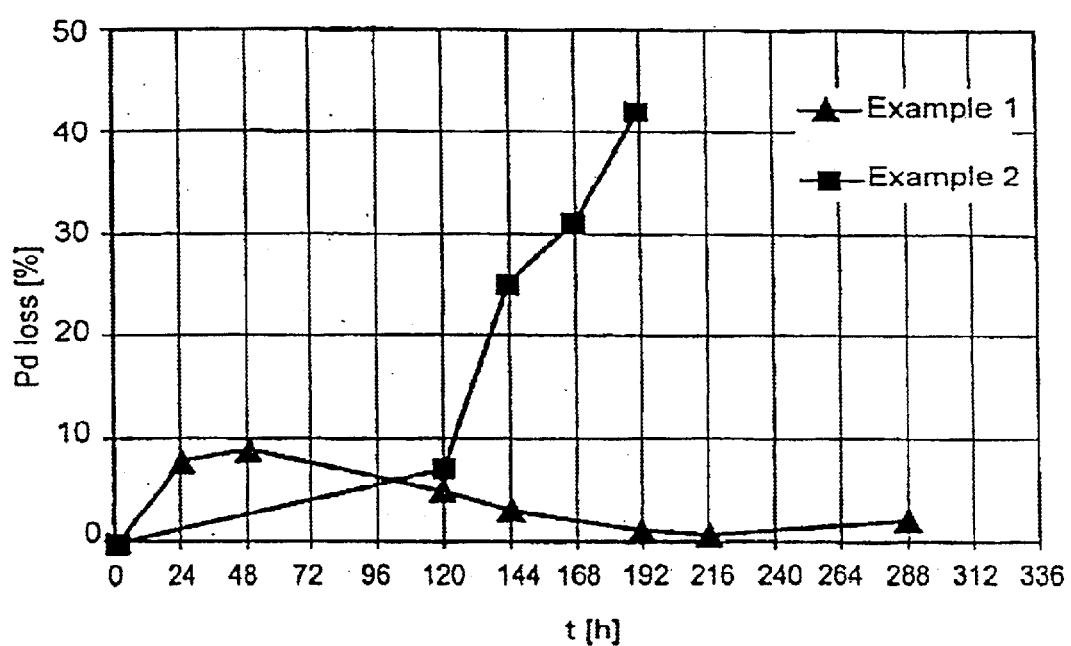
FIG. 1 graphically depicts the results of Example 1 and Example 2.

The parameters referred to in this document are, unless stated otherwise, as defined below, with PAc being propionic acid and PAn being propionic anhydride.

Selectivity (PAc):
S(PAc)=PAc produced [mol]/{PAc produced [mol]+ethane produced [mol]+diethyl ketone produced [mol]+ propionaldehyde produced [mol]}

Space-Time Yield (PAc):
STY(PAc)=PAc produced [g]/{reaction volume [l]×time [h]}

Space-Time Yield(PAn):
STY(PAn)=PAn produced [g]/{reaction volume [l]×time [h]}

Turnover Frequency:
TOF={PAc produced [mol]+PAn produced [mol]}/{amount of palladium [mol]×time [h]}

Preparation of Component A (Amidated Polyethylenimine)

500 g of Polymin® WF (from BASF Aktiengesellschaft) were placed in a reaction vessel. Polymin® WF is a polyethylenimine polymer having a weight average molecular weight of about 25,000 g/mol. 500 g correspond to about 11.6 mol of ethylenimine units. About 75% of the nitrogen atoms present can in principle be amidated by means of carboxylic acids, while the remaining 25% are tertiary amine groups.

At 130° C., 646 g (8.72 mol) of propionic acid were added dropwise under a gentle stream of nitrogen over a period of 2 hours. The temperature was subsequently increased to 160° C. and the water of reaction was distilled off, with about 34 g of the propionic acid added (0.46 mol) being entrained with the water. After 4 hours, this amount of propionic acid was added again and the reaction mixture was heated at 180° C. for 15 hours. After cooling, 964 g of a polyethylenimine amidated by propionic acid was obtained as a yellow-red solid, hereinafter referred to as "Polymin-PS".

Preparation of Component B (Diphosphine Ligand dpa-3)

The starting material 1,3-diphosphinopropane was obtained by the method of R. W. Alder et al., J. Chem. Soc., Perkin Trans. I, 1998, pages 1643 to 1655 by reacting 1,3-dibromopropane with triethyl phosphite to form 1,3-bis (diethoxyphosphinyl)propane and subsequently reducing the isolated intermediate by means of lithium aluminum hydride.

The preparation of the diphosphine ligand 1,3-P,P'-di(2-phospha-1,3,5,7-tetramethyl-6,9,10-trioxatricyclo [3.3.1.1{3.7}]decyl)propane, hereinafter referred to as "dpa-3", was carried out using a method analogous to Example 1 of WO 98/42717. 4.63 mmol of 1,3-diphosphinopropane were added to a solution of 27.8 mmol of 2,4-pentanedione in 20 ml of 5M aqueous hydrochloric acid and the mixture was stirred. After about one hour, precipitation of a white solid commenced. After a further 24 hours, the volatile constituents were removed and the white product was washed with water (6×20 ml), taken up in 20 ml of dichloromethane and dried over magnesium sulfate. After drying, the desiccant was filtered off and the solution was evaporated to about 1 ml under reduced pressure. Addition of 10 ml of anhydrous pentane resulted in renewed formation of a white precipitate of "dpa-3" which was separated off and freed of remaining solvent.

Experimental Procedure 1

The starting components of the catalyst system (palladium compound, phosphine, solubilizable nitrogen-containing polymer if used and any activator used) were dissolved in degassed aqueous propionic acid under an argon atmosphere and transferred under an argon atmosphere to an autoclave. The autoclave was closed and a pressure of 0.6 MPa abs was set by means of a carbon monoxide/ethene gas mixture having a molar ratio of 1:1. The reaction mixture was subsequently heated to the desired reaction temperature and a pressure of 1.1 MPa abs was set by injection of further carbon monoxide/ethene gas mixture (molar ratio 1:1). The pressure was kept constant over the total time of the test by injection of further gas mixture. After one hour, the reaction mixture was cooled to room temperature, the autoclave was vented and the reaction mixture was discharged under an argon atmosphere. The composition of the reaction mixture and the gas phase were determined by gas chromatography and by wet chemical methods, respectively.

Example 1

Stability of the Catalyst System

A solution of 0.87 g of tetrakis(triphenylphosphine) palladium ($Pd(PPh_3)_4$), 1.97 g of triphenylphosphine ($PPh_3$) and 3 g of "Polymin-PS" (component A) in 97 ml of 98% strength aqueous propionic acid was transferred under an argon atmosphere into an autoclave and stirred at 110° C. under 0.6 MPa abs of a carbon monoxide atmosphere for 12 days. To determine the palladium content of the solution, samples were taken during the experiment and analyzed by atomic absorption spectroscopy (AAS).

The results are shown graphically in FIG. 1. No deposition of palladium was observed during the experiment. 98% of the palladium used were still found in the solution after the end of the experiment after 288 hours.

Example 2

Carbonylation of Ethene, According to the Present Invention 55 g of the reaction solution which had been pretreated thermally with carbon monoxide as described in Example 1 were admixed with 4 g of water and 1.5 g of triphenylphosphine ($PPh_3$), pressurized with a carbon monoxide/ethene gas mixture and treated as described in experimental procedure 1. The reaction temperature was 110° C. Propionic acid was formed in a space-time yield of 87 g/l·h and a selectivity of over 99%. The calculated TOF was 170 $h^{-1}$.

Example 3

Carbonylation of Ethene, According to the Present Invention

In a control experiment, a reaction solution of 0.17 g of palladium acetate, 1.97 g of triphenylphosphine ($PPh_3$) and 3 g of "Polymin-PS" (component A) in 97 ml of 90% strength aqueous propionic acid was freshly made up and not pretreated with carbon monoxide. This was then treated with a carbon monoxide/ethene gas mixture at 110° C. under conditions as described under experimental procedure 1 to give propionic acid in a space-time yield of 80 g/l·h and a selectivity of over 99%. The calculated TOF was 145 $h^{-1}$.

Comparison of Example 2 with Example 3 shows that the catalyst system stabilized with the solubilized nitrogen-containing polymer "Polymin-PS" after exposure for 12 days to a reducing carbon monoxide atmosphere at elevated temperature and a further addition of triphenylphosphine still has a high activity and selectivity comparable to that of a freshly prepared catalyst system which has not been pretreated with carbon monoxide.

Example 4

Stability of the Catalyst System

A solution of 0.34 g of palladium acetate and 3.81 g of triphenylphosphine (PPh$_3$) in 200 ml of 98% strength aqueous propionic acid was transferred under an argon atmosphere into an autoclave and stirred at 110° C. under 0.6 MPa abs of a carbon monoxide atmosphere for 8 days. The palladium content of the solution was determined as in Example 1 by means of AAS.

The results are shown graphically in FIG. 1. After 120 hours, deposition of elemental palladium was observed. Only about 60% of the palladium used was found in the solution after the end of the experiment after 192 hours.

Example 1 shows that in the presence of "Polymin-PS" the catalyst system is stabilized very effectively, no deposition of elemental palladium takes place and the palladium content of the solution is virtually fully maintained even after a number of days. In contrast, deposition of elemental palladium and a significant decrease in the palladium content of the solution was observed after only 5 days in the absence of the solubilized nitrogen-containing polymer "Polymin-PS".

Example 5

Stability of the Catalyst System

The starting compound [Pd(dpa-3)(CH$_3$CN)$_2$][OTs]$_2$ of the catalyst system was prepared by gradual reaction of palladium acetate with "dpa-3" (component B) and p-toluenesulfonic acid (TsOH) in acetonitrile at room temperature. A solution of 0.8 g of [Pd(dpa-3)(CH$_3$CN)$_2$][OTs]$_2$ (0.8 mmol) and 2.1 g of "Polymin-PS" (component A) in 68 ml of 98% strength aqueous propionic acid was transferred under an argon atmosphere into an autoclave and stirred at 110° C. under 0.6 MPa abs of a carbon monoxide atmosphere for 5 days. The palladium content of the solution was determined as in Example 1 by means of AAS.

Figure 2:
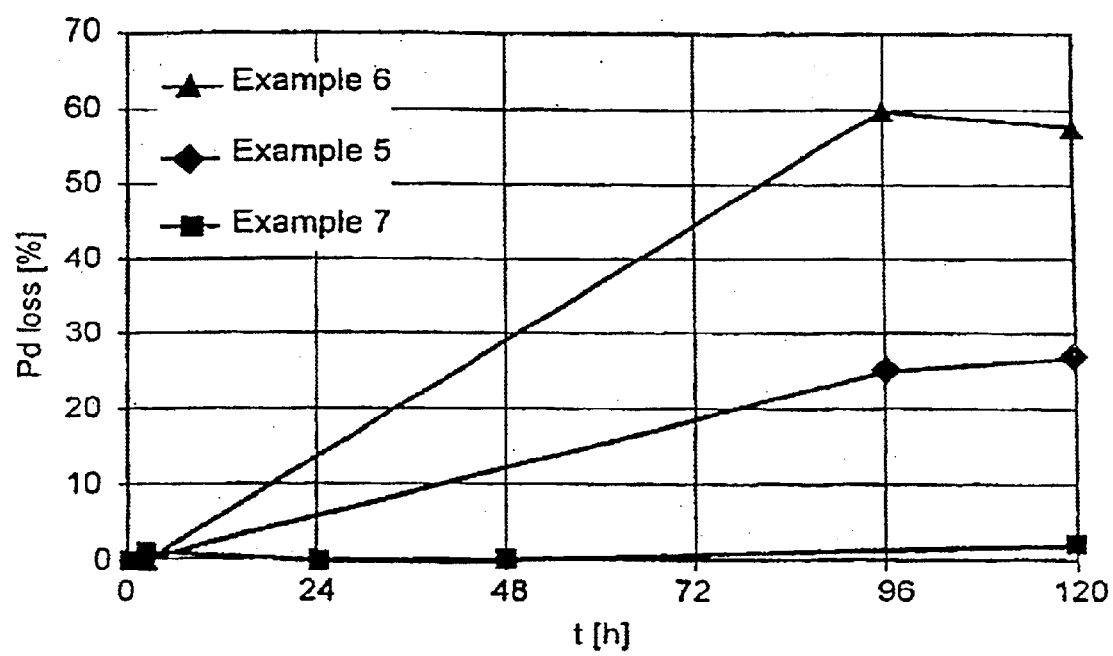
FIG. 2 graphically depicts the results of Example 5, Example 6, and Example 7.

The results are shown graphically in FIG. 2. After 96 hours, deposition of elemental palladium was observed. About 75% of the palladium used was found in the solution after the end of the experiment after 120 hours.

Example 6

Stability of the Catalyst System

Example 6 was carried out without addition of "Polymin-PS", but otherwise under conditions identical to Example 5.

The results are shown graphically in FIG. 2. After 96 hours, deposition of elemental palladium was observed. Only about 40% of the palladium used was found in the solution after the end of the experiment after 120 hours.

Example 7

Stability of the Catalyst System

Example 7 was carried out with a further addition of 0.67 g of "dpa-3" (1.4 mmol, component B), but otherwise under conditions identical to Example 5.

No deposition of palladium was observed during the experiment. Over 95% of the palladium used was found in the solution after the end of the experiment after 120 hours.

Comparison of Examples 5 and 6 shows that the presence of a solubilized nitrogen-containing polymer ("Polymin-PS") significantly increases the stability of the catalyst system and counters deposition of elemental palladium. Increasing the "dpa-3"/palladium ratio from 1.0 in Example 5 to 2.75 in Example 7 leads in the presence of "Polymin-PS" to a very stable catalyst system in which no deposition of elemental palladium was observed even after 5 days and over 95% of the palladium used could be found in the solution after this time.

Example 8

Carbonylation of Ethene, According to the Present Invention 0.17 g of palladium acetate, 1.97 g of triphenylphosphine (PPh$_3$) and 3 g of "Polymin-PS" (component A) were dissolved in 95 ml of degassed 98% strength aqueous propionic acid under an argon atmosphere. The proportion of "Polymin-PS" was 3% by weight, and the proportion of water was 2% by weight, in each case based on the total liquid reaction mixture. The solution was subsequently pressurized with carbon monoxide/ethene gas mixture and treated as described in experimental procedure 1. The reaction temperature was 130° C.

The water content of the product was 0.0% by weight, based on the total liquid reaction product. The STY(PAc) was 58 g/l·h, and the STY(PAn) was 160 g/l·h. This corresponds to a TOF of 260 h$^{-1}$.

Example 9

Carbonylation of Ethene, Comparative Example

Example 9 was carried out without addition of "Polymin-PS", but otherwise under conditions identical to Example 8.

The water content of the product was 0.2% by weight, based on the total liquid reaction product. The STY(PAc) was 42 g/l·h, and the STY(PAn) was 90 g/l·h. This corresponds to a TOF of 170 h$^{-1}$.

Example 8 shows that a significantly higher STY of propionic acid and propionic anhydride is achieved in the presence of the solubilized nitrogen-containing polymer "Polymin-PS" than in Example 9 without addition of a solubilized nitrogen-containing polymer.

Example 10

Carbonylation of Ethene, According to the Present Invention 0.17 g of palladium acetate, 1.97 g of triphenylphosphine (PPh$_3$), 3 g of "Polymin-PS" (component A) and 2.2 g of phosphoric acid as activator were dissolved in 93 ml of degassed 97.5% strength aqueous propionic acid under an argon atmosphere. The proportion of "Polymin-PS" was 3% by weight, the proportion of water was 2% by weight and the proportion of phosphoric acid was 2.3% by weight, in each case based on the total liquid reaction mixture. The solution was subsequently pressurized with carbon monoxide/ethene gas mixture and treated as described in experimental procedure 1. The reaction temperature was 130° C.

The water content of the product was 0.0% by weight, based on the total liquid reaction product. The STY(PAn) was 260 g/l·h. Since, owing to the high reaction rate to propionic anhydride, about 7.8% of the propionic acid present as starting material were additionally consumed, the STY(PAc) was not calculated. The calculated TOF was 410 h$^{-1}$.

Example 11

Carbonylation of Ethene, Comparative Example

Example 11 was carried out without addition of "Polymin-PS", but otherwise under conditions identical to Example 10.

The water content of the product was 0.1% by weight, based on the total liquid reaction product. The STY(PAc) was 98 g/l·h. The calculated TOF was 170 h$^{-1}$.

Example 10 shows that the presence of the solubilized nitrogen-containing polymer "Polymin-PS" and a strong acid as activator results in a very high reaction rate which under the prevailing reaction conditions led to further reaction of the propionic acid formed and initially present to propionic anhydride. In the absence of the solubilized nitrogen-containing polymer "Polymin-PS" (Example 11), a significantly lower reaction rate was achieved.

Examples 8 to 11 show that both the addition of a solubilized nitrogen-containing polymer and the addition of a strong acid as activator have a decisive influence on the reaction rate and the yield of desired products. By far the best results were achieved in the presence of both additives (solubilizable nitrogen-containing polymer and strong acid as activator).

Example 12

Carbonylation of Ethene, Comparative Example 22 mg of palladium acetate (0.1 mmol) and 57 mg of "dpa-3", (0.12 mmol, component B) were dissolved in 100 ml of degassed 90% strength aqueous propionic acid under an argon atmosphere. The solution was subsequently pressurized with carbon monoxide/ethene gas mixture and treated as described in experimental procedure 1. The reaction temperature was 100° C. The reaction produced propionic acid in an STY(PAc) of 110 g/l·h and a selectivity of over 99%. The calculated TOF was 1600 h$^{-1}$.

Example 13

Carbonylation of Ethene, According to the Present Invention 22 mg of palladium acetate (0.1 mmol), 142 mg of "dpa-3" (0.3 mmol, component B) and 7.5 g of "Polymin-PS" (component A) were dissolved in 87.5 ml of degassed 85% strength aqueous propionic acid under an argon atmosphere. The solution was subsequently pressurized with carbon monoxide/ethene gas mixture and treated as described in experimental procedure 1. The reaction temperature was 100° C. The reaction produced propionic acid in an STY(PAc) of 345 g/l·h and a selectivity of over 99%. The calculated TOF was 4800 h$^{-1}$.

Example 14

Carbonylation of Ethene, According to the Present Invention

Example 14 was carried out by a method analogous to Example 13 using 22 mg of palladium acetate (0.1 mmol), but using 57 mg of "dpa-3" (0.12 mmol, component B) and 3 g of "Polymin-PS" (component A). The reaction produced propionic acid in an STY(PAc) of 340 g/l·h and a selectivity of over 99%. The calculated TOF was 4800 h$^{-1}$.

Examples 13 and 14 show that a very high space-time yield of propionic acid of significantly above 300 g/l·h is obtained in the presence of the bidentate phosphine ligand "dpa-3" and the solubilized nitrogen-containing polymer "Polymin-PS".

Example 15

Carbonylation of Ethene, Comparative Example 2 g of a supported catalyst comprising 5% by weight of Pd on activated carbon and 57 mg of "dpa-3" (0.12 mmol, component B) were suspended/dissolved in 100 ml of degassed 85% strength aqueous propionic acid under an argon atmosphere. The mixture was subsequently pressurized with carbon monoxide/ethene gas mixture and treated as described in experimental procedure 1. The reaction temperature was 110° C. The reaction produced propionic acid in an STY(PAc) of only 26 g/l·h and a selectivity of 95%.

Example 16

Carbonylation of Ethene, According to the Present Invention

Example 16 was carried out by a method analogous to Example 15 using 2 g of a supported catalyst comprising 5% by weight of Pd on activated carbon and 57 mg of "dpa-3" (0.12 mmol, component B), but additionally using 5 g of "Polymin-PS" (component A). The reaction produced propionic acid in an STY(PAc) of 460 g/l·h and a selectivity of over 99%.

Example 16 shows that the palladium component used can also be immobilized on a heterogeneous support. Comparison with Example 15 makes clear the significant effect of the solubilized nitrogen-containing polymer. In the presence of "Polymin-PS" in Example 16, the space-time yield of propionic acid was a factor of 18 higher than in Example 15.

What is claimed is:

1. A catalyst system for the carbonylation of olefinically or acetylenically unsaturated compounds by means of carbon monoxide and a nucleophilic compound, comprising
   (a) palladium,
   (b) a phosphine, and
   (c) a polyethylenimine.

2. A catalyst system as claimed in claim 1 in which the polyethylenimine is a polyethylenimine comprising units of the formula (I) or branched isomers thereof

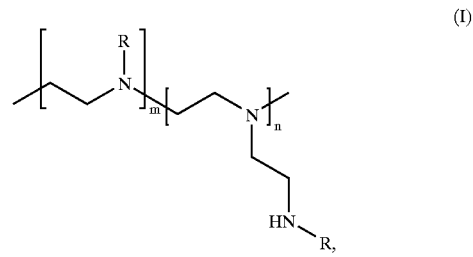

where the sum m+n is at least 10 and R are, independently of one another, hydrogen, alkyl, cycloalkyl, aryl, aralkyl and acyl radicals having up to 30 carbon atoms or hydroxyalkyl (poly)oxyalkylene radicals having up to 500 oxyalkylene units.

3. A catalyst system as claimed in claim 2 comprising a polyethylenimine (I) in which the radicals R are identical or different acyl radicals having up to 30 carbon atoms.

4. A catalyst system as claimed in claim 1 in which the polyethylenimine is present in an amount of from 0.5 to 15% by weight, based on the total mass of the reaction mixture.

5. A catalyst system as claimed in claim 1 in which the phosphine is an at least bidentate phosphine.

6. A process for the carbonylation of olefinically or acetylenically unsaturated compounds by means of carbon monoxide and a nucleophilic compound, wherein a catalyst system comprising (a) palladium, (b) a phosphine, and (c) a polyethylenimine is used.

7. A process as claimed in claim 6, wherein the carbonylation is carried out at from 50 to 150° C. and a pressure of from 0.1 to 5 MPa abs.

8. A process as claimed in claim 6, wherein the olefinically unsaturated compound used is ethene.

9. A process as claimed in claim 6, wherein the nucleophilic compound used is water, a $C_2$–$C_{10}$-carboxylic acid and/or a $C_1$–$C_{10}$-alkanol.

10. A process as claimed in claim 6, wherein the nitrogen-containing polymer used is a polyethylenimine (I) in which the radicals R are acyl groups which correspond to the carboxylic acid derivative to be prepared.

11. A process as claimed in claim 6, wherein the polyethylenimine is a polyethylenimine comprising units of the formula (I) or branched isomers thereof

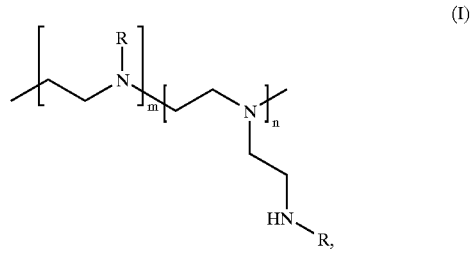

(I)

where the sum m+n is at least 10 and R are, independently of one another, hydrogen, alkyl, cycloalkyl, aryl, aralkyl and acyl radicals having up to 30 carbon atoms or hydroxyalkyl (poly)oxyalkylene radicals having up to 500 oxyalkylene units.

* * * * *